United States Patent [19]

Kobayashi et al.

[11] 4,237,878
[45] Dec. 9, 1980

[54] DRIPPING FLUID LEVEL DETECTOR

[75] Inventors: Toshiyuki Kobayashi, Kyoto; Hideharu Nakai, Nagaokakyo; Isao Kai, Kameoka; Yoshinori Yonemori, Tokyo, all of Japan

[73] Assignees: Omron Tateisi Electronics Co., Ltd., Kyoto, Japan; Bohsei Enterprise, Tokyo, Japan

[21] Appl. No.: 799

[22] Filed: Jan. 3, 1979

[30] Foreign Application Priority Data

Jan. 10, 1978 [JP] Japan .................. 53/1302
Jan. 10, 1978 [JP] Japan .................. 53/1305

[51] Int. Cl.$^3$ ............................ A61M 5/14
[52] U.S. Cl. .................. 128/214 E; 128/DIG. 13; 222/23; 340/620
[58] Field of Search ....... 128/214 E, 214 F, DIG. 12, 128/DIG. 13, 227; 340/562, 603, 606, 609, 620; 222/23

[56] References Cited

U.S. PATENT DOCUMENTS

| 3,450,153 | 6/1969 | Hildebrandt et al. ... 128/DIG. 13 X |
| 3,500,366 | 3/1970 | Chesney et al. ............. 128/214 E X |
| 3,743,865 | 7/1973 | Reichmann .......................... 340/562 |
| 3,992,706 | 11/1976 | Tunney et al. ............. 128/214 E X |
| 4,002,996 | 1/1977 | Klebanoff et al. ............ 128/214 E X |
| 4,105,028 | 8/1978 | Sadlier et al. ..................... 340/609 X |

Primary Examiner—William E. Kamm
Attorney, Agent, or Firm—Stevens, Davis, Miller & Mosher

[57] ABSTRACT

Disclosed is a dripping fluid level detector comprising a pair of electrodes oppositely disposed around a drip chamber of a supply passage of dripping medical fluid and a detecting circuit which detects the remaining amount of medical fluid according to changes in the electrostatic capacity caused between said pair of electrodes.

7 Claims, 10 Drawing Figures

Electrostatic capacity of electrodes (PF)

DRIPPING FLUID LEVEL DETECTOR

The present invention relates to a dripping fluid level detector employed within a medical fluid dropper or instillator, which detects the remaining amount of medical fluid when the medical fluid is dripped downwardly through a dripping chamber from a medical fluid bottle provided above into a vein or vessel of a human body undergoing a surgical operation at a hospital or the like.

There is known a medical fluid dropper which comprises a bottle, tank or container containing medical fluid, a conduit, passage or tube to be connected between the bottle and the vein of a human body undergoing the surgical operation, and a dripping chamber provided within the tube for controlling or administrating the dripping of medical fluid drop by drop through the tube from the bottle into the vein of the human body. In such a medical fluid dropper, if the medical fluid runs out during the dripping operation, the body fluid flows from the human body into the tube, resulting in an extremely dangerous situation for the human body. Conventionally, the patient or the doctor observes the amount of medical fluid remaining in the medical fluid dropper and notifies a nurse in charge when the remaining fluid is reduced to a small amount. This procedure is complicated for the observer and insufficient in safety for the patient. Thus, several types of dripping fluid level detectors for detecting the remaining amount within the medical fluid dropper, as described hereinafter, have been proposed.

Firstly, two injection needles are inserted into the rubber plug of a medical fluid bottle and a voltage is applied between the two injection needles to detect whether or not current flows between them. Since the medical fluid is conductive, current flows to the medical bottle when medical fluid there is remaining, and the current does not flow when no medical fluid remains.

Secondly, the remaining amount of the medical fluid in the bottle is weighed to make the detection through a weight measurement.

Thirdly, the detection is made according to change in light amount transmitted through the medical fluid bottle by use of a photoelectric switch.

However, with the first detector, since the electric resistance of human body fluid is extremely small, the electric current may flow into the human body of the patient through the one end of the transfusion tube inserted into the vein of the patient. In addition thereto, the handling procedure for the injection needles becomes complicated, because the injection needle must be sterilized. With the second detector, a regulation has to be made according to the specific gravity of the medical fluid, since the specific gravity thereof is variable. Thus, the handling operation for the weight measurement becomes complicated and the errors are very likely. Also, in the third detector, the regulation for the light amount is difficult to obtain, since the color of the medical fluid is different for different fluids with light being a variable transmission factor. Moreover, if the medical fluid remains attached as drips to the detected location in connection with the photoelectric switch, an error may be caused.

An object of the present invention is to provide a dripping fluid level detector, which is higher in reliability, easier to handle and sufficiently safe, and which eliminates the disadvantages inherent in conventional dripping fluid detectors.

Another object of the present invention is to provide a dripping fluid level detector, which is free from errors caused by an increase in electrostatic capacity due to the approach of a human body or the like to the medical fluid dropper.

According to the present invention, the above described objects can readily be accomplished by providing a dripping fluid level detector of an electrostatic capacity type comprising a pair of electrodes disposed at a given location along the medical fluid passage of the medical fluid dropper, which is composed of a bottle, drip chamber, transfusion tube, bottle needle, etc., said drip chamber being grasped between the electrodes, thereby to detect the dripping fluid level according to a change in the electrostatic capacity caused between the electrodes.

These and other objects and features of the present invention will become apparent from the following description taken in conjunction with preferred embodiments thereof with reference to the accompanying drawings, in which:

FIG. 1 is a perspective view of a level detector employed within a medical fluid dropper showing one preferred embodiment of the present invention;

FIGS. 2 (a) and 2 (b) are perspective views of the level detector in FIG. 1 showing the opened and closed positions thereof, respectively;

Before the description of the present invention proceeds, it is to be noted that like parts are designated by like reference numerals throughout the accompanying drawings.

Figure 1:
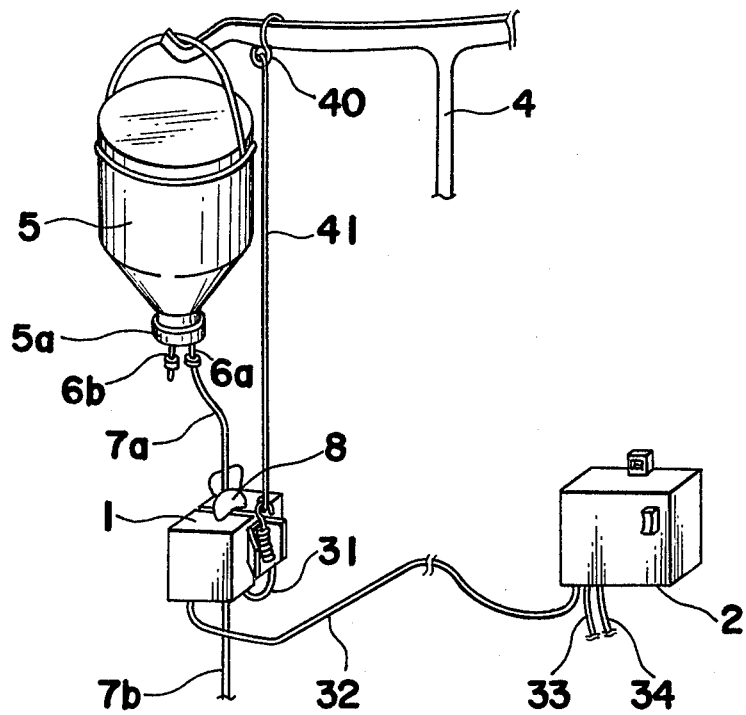

Referring to FIG. 1, there is shown a medical fluid dropper comprising a bottle 5 for containing medical fluid, a transfusion fluid tube 7 connected between the bottle 5 and the vein of a human body who is undergoing the surgical operation, a drip chamber 8 provided within the intermediate portion of the tube 7a and 7b for controlling the dripping of medical fluid drop by drop through the tube 7 from the bottle 5 to the vein of the human body, a level detector including a head 1 provided with a pair of electrodes 14a, 14b oppositely disposed around the dripping chamber 8 for detecting the electrostatic capacity existing between the electrodes 14a, 14b and an electric circuit including a control circuit 2 connected between the electrodes 14a, 14b and a constant voltage power source for generating an output signal in accordance with the changing of the electrostatic capacity of the electrodes 14a, 14b, and a suspending structure including a stand 4 for supporting the bottle 5 at the upper portion and the level detector 1 at the middle position in such a manner that the medical fluid may flow downwardly by the gravity of itself from the bottle 5 and through the other end of the tube 7 connected to the vein of a human body through the drip chamber 8. The amount of medical fluid remaining may be detected by means of the level detector 1 according to changes in the electrostatic capacity caused between said pair of electrodes 14a and 14b.

Figure 4:
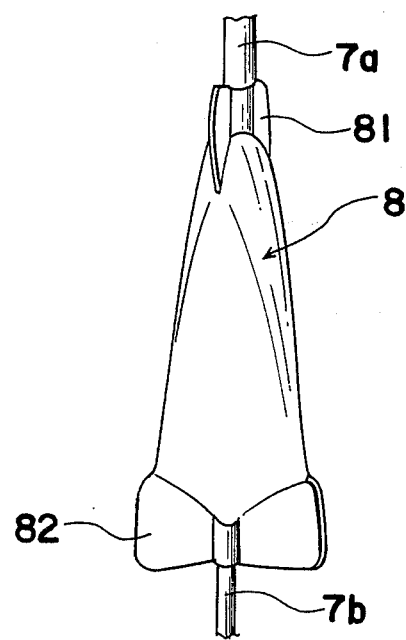
FIG. 4 is a perspective view showing a drip chamber employed in the medical dropper of FIG. 1.

In FIG. 1, the bottle 5 is suspended from the stand 4 for dripping use and is filled with the given medical fluid. The different types of medical fluids which may be filled within the bottle 5 are approximately equal in specific dielectric constant which is relatively large in comparison with other materials. A rubber plug 5a is mounted into the lower opening of the medical fluid bottle 5, through which an air needle 6b and a bottle needle 6a are projected into the bottle 5. An upper tube 7a which is made of an insulating resin is connected, at its one end, to the bottle needle 6a. As shown in FIG. 4, the drip chamber 8 of an insulating synthetic resin is formed into a bag shape. Since the top end 81 and bottom end 82 of the drip chamber 8 extend at a right angle with respect to each other, forming a rib shape, the shape of the drip chamber 8 is a slightly complicated tetrahedron on the whole. The other end of the upper fluid tube 7a and one end of a lower tube 7b of the similar insulating resin are connected, respectively, to the top end 81 of the drip chamber 8 and the bottom end 82 thereof. The other end (not shown in drawings) of the lower tube 7b is inserted into the vein of a human body of a patient. The drip chamber 8, the transfusion fluid tubes 7a, 7b, the bottle needle 6a, etc. combined forms a dripping set as one unit. They are approximately uniformed in shape, size and material quality in practical use.

The detection head 1 is detachably mounted on the drip chamber 8 as described hereinafter. The detection head 1 is connected with a signal cable 32 to the control circuit 2 which is connected through cables 33 and 34 to a central control panel unit 24 including a warning circuit (not shown) for generating a warning signal in accordance with the detection output of the control circuit 2.

Figure 2A:
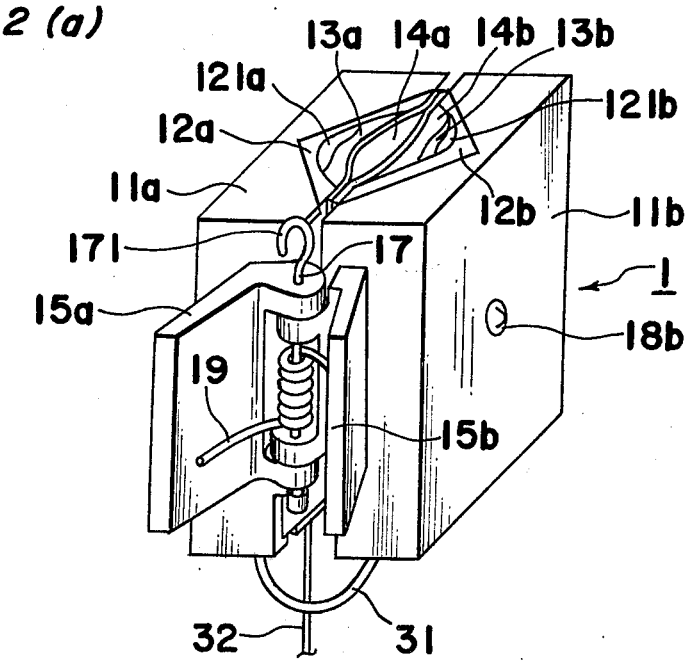
Figure 2:
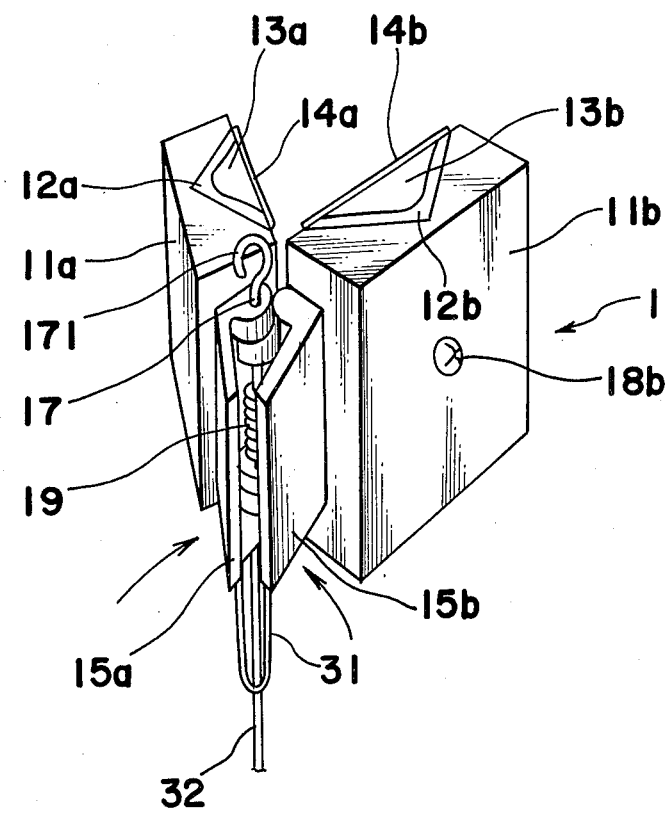
Figure 3:
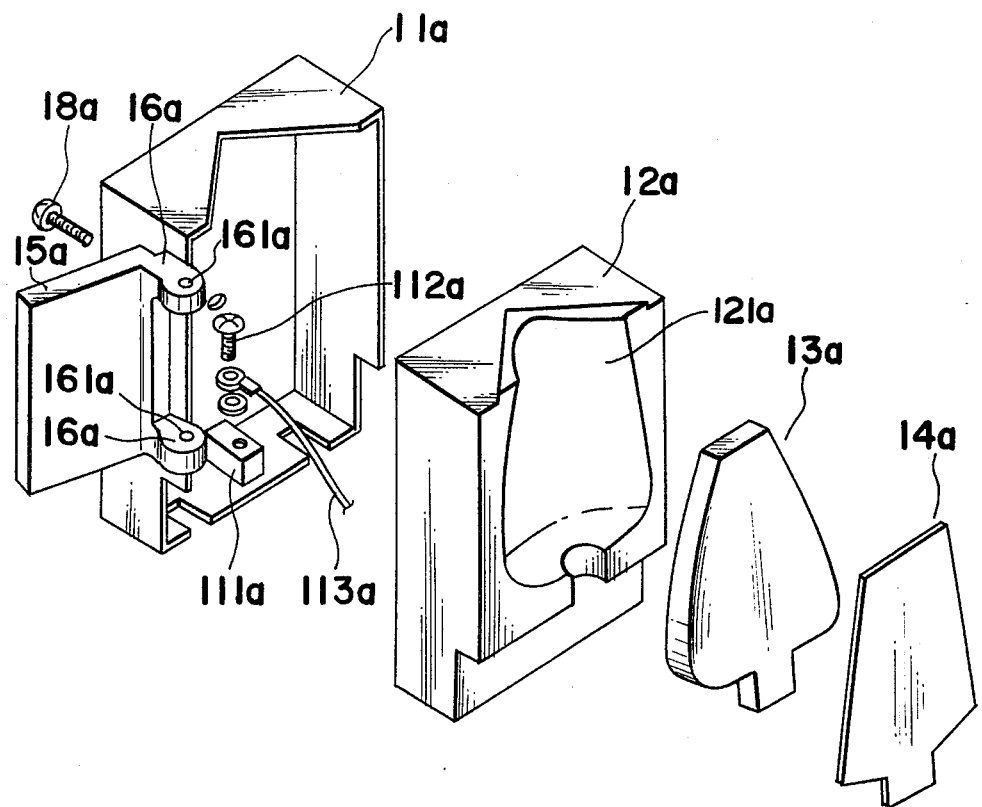
FIG. 3 is an exploded perspective view showing the parts of the level detector in FIG. 2.

Referring to FIGS. 2 (a) and 2 (b), the detection head 1 is composed of a pair of covers 11a, 11b each accompanying with an electrode fixture 12a or 12b, buffer member 13a or 13b, electrode 14a or 14b and spring holder 15a or 15b, a stem 17, and a torsion coil spring provided between said pair of the covers 11a, 11b. Since the covers have the identical construction with each other, for the sake of brevity, one of the covers 11a and 11b will be described in detail hereinbelow with reference to FIG. 3. The cover 11a made of a synthetic resin has the configuration of a box shape with its one face being open and the other surface being entirely plated. A lead wire 113a is mounted, by a screw 112a, to the connecting portion 111a provided on the inside of the cover 11a. The spring holder 15a for a spring 19 and two hole-members 16a, 16a for a stem 17 are integrally formed on the outside of the cover 11a. Both of the hole members 16a and 16a have holes 161a, 161a formed therein respectively, the stem 17 being adapted to extend through the holes 161a, 161a. The electrode fixture 12a made of an insulating synthetic resin is adapted, in shape, to be accommodated within the opened face of the cover 11a and secured to the cover 11a with a screw 18a, and a concave portion 121a is formed in the electrode fixture 12a. The buffer member 13a composed of spongy synthetic resin is mounted in the concave portion 121a with a bonding agent or the like. The electrode 14a made of conductive soft resin, that is, of an elastic deformable substance is mounted on the buffer member 13a with the bonding agent or the like.

The other cover 11b associated with the electrode fixture 12b, the buffer member 13b, the electrode 14b, the spring holder 15b, hole members 16b, 16b and a screw 18b sets in a pair with the above described cover 11a as a pair of pincers and has the almost same configuration as that of the cover 11a including the electrode fixture 12a, the buffer member 13a, the electrode 14a, the spring holder 15a, the hole members 16a, 16a and a screw 18a. However, the space between the hole members 16b and 16b is narrower than the space between the hole members 16a and 16a so that the hole members 16b and 16b are interlocked between the hole members 16a and 16a. If the torsion coil spring 19 is disposed between the hole members 16b, 16b and the stem 17 is extended through the hole members 16a, 16b, 16b, 16a and coil spring 19, the spring holders 15a, 15b are rotatably supported by the stem 17 and are urged to be repelled with respect to each other by the resilient force of the torsion coil spring 19. In other words, the covers 11a, 11b are rotatably supported by the stem 17 and are urged, by the spring 19, to approach with respect to each other through the spring holders 15a, 15b. The spring holders 15a, 15b are disposed to be held as one unit between the fingers of the operator. The one end of the stem 17 is formed of a hook-shaped swing portion 171 for suspending the head 1 onto the suspending structure.

Figure 5:
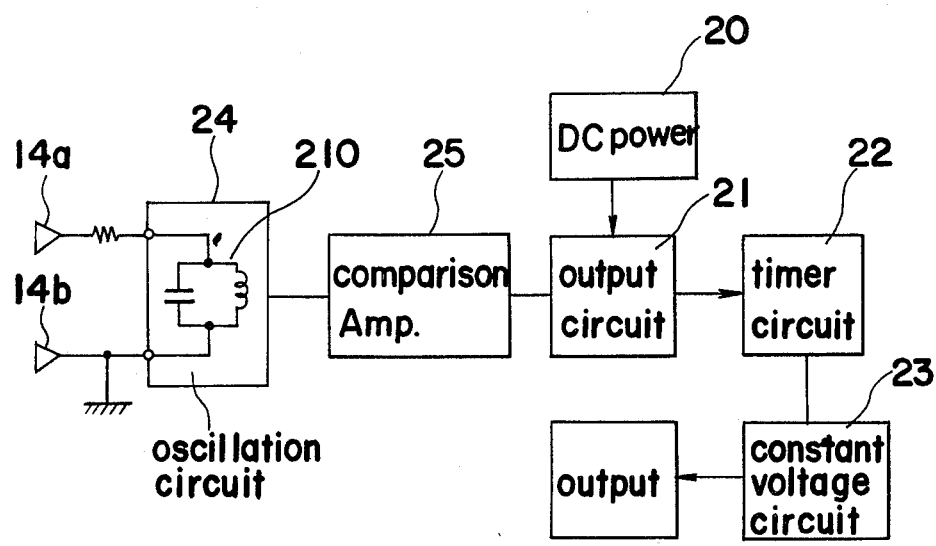
FIG. 5 is a block diagram of the electric circuit employed within the level detector of FIG. 2.

The construction of the control circuit 2 will be described hereinafter. The control circuit 2 generates an electric detection output according to the variation of the electrostatic capacity existing between the electrodes 14a and 14b. The control circuit can be variably constructed and is preferable to be constructed as shown in, for example, FIG. 5. Referring to FIG. 5, the control circuit is composed of a DC power supply 20 composed of a battery cell, an output circuit 21, a timer circuit 22, a constant-voltage circuit 23, an oscillation circuit 24 and a comparison amplification circuit 25. The oscillation circuit 24 is accommodated in a predetermined location of the above-described electrode fixture 12a and the other circuit portions are accommodated in the control circuit 2. The one electrode 14a is directly connected to the oscillation circuit 24 provided with LC resonance circuit 210, while the other electrode 14b is connected to the oscillation circuit 24 through the signal cable 31. A signal cable 31 as shown in FIG. 1 and FIGS. 2 (a) and 2 (b) is designed to connect the electrode 14b to the resonance circuit 210. The electrostatic capacity caused between the electrodes 14a and 14b is applied to actuate the resonance circuit of the oscillation circuit 24 which is connected in series with the comparison amplification circuit 25, output circuit 21 with DC power supply 20, timer circuit 22 and constant voltage circuit 23.

The operation of the medical fluid dropper constructed as mentioned hereinabove will be described hereinafter. Referring to FIG. 1 and FIGS. 2 (a) and 2 (b), the medical fluid bottle 5 is sufficiently filled with the medical fluid. The medical fluid drips drop by drop to the drip chamber 8 through the upper transfusion tube 7a. Approximately the half portion of the drip chamber 8 is adapted to be normally filled with the medical fluid and the dripped amount per time unit can be obtained from the dripping rate in the drip chamber 8. The medical fluid drips further through the lower transfusion tube 7b into the vein of the human body.

After the adjustment of the dripped amount, etc. has been completed in a known manner, the detection head 1 is mounted on the drip chamber 8. Namely, the spring holders 15a and 15b are integrally held between the fingers of the operator to carry the detection head 1 to the drip chamber 8 so that the spring holders 15a and 15b of the detection head are depressed against the resilient force of the coil spring to approach towards each other, thereby to open the covers 11a, 11b together with the electrodes 14a and 14b, as shown in FIG. 2 (b). When the electrodes 14a, 14b open at a given angle, the drip chamber 8 is disposed to be provided, in its bottom portion, between the electrodes 14a and 14b. Then, the depression of the spring holders 15a and 15b is released and, thus, the drip chamber 8 is grasped between the electrodes 14a and 14b of the detection head 1, as shown in FIG. 1 and FIG. 2 (a). As a result, the detection head 1 is securely suspended on the drip chamber 8. On the other hand, the outer face of the drip chamber 8 has thrust into the concave portions 121a and 121b, compressing the buffer members 13a and 13b, whereby the electrodes 14a and 14b sufficiently fit and directly attach with the outer face of the drip chamber 8 regardless of the complicated shape of the outer face of the drip chamber 8. Since the electrodes 14a and 14b are formed of an elastic substance, they conform to the contours of drip chamber 8.

To disengage the detection head 1 from the drip chamber 8, the spring holders 15a and 15b are depressed by fingers of the operator to open the electrodes 14a and 14b at a given angle and, the detection head 1 is required to be separated away from the drip chamber 8 while the spring holders 15a, 15b as they are being integrally held.

A suspension cord 41 is employed to connect at its one end, to the swing portion 171 of the stem 17 and at its other end, to the pawl portion 40 of the stand 4 for dripping and is adjusted in its length so that it may not be loosened. Thus, the load of the detection head 1 is applied upon the suspension cord 40, instead of the dripping set, to prevent accidents such as pulling out of the bottle needle 6a from the rubber plug of the bottle 5 through the tube 7. However, when the level of the dripping fluid is not detected, the swing portion 171 can be engaged with the pawl portion 40, etc. for custody. Also, the swing portion 171 is provided to prevent the stem 17 from being pulled out.

Thus, after the detection head 1 has been mounted on the drip chamber 8, the level detecting operation of the dripping fluid within the drip chamber 8 is made to be performed by means of the detection head 1. Since the electrodes 14a, 14b fit the drip chamber 8 perfectly, the electrostatic capacity between the electrodes 14a and 14b changes with high sensitivity in accordance with changes in the medical fluid amount of the drip chamber 8. Referring to FIG. 5, the Q value of the resonance circuit 210 changes with changes in the electrostatic capacity and the oscillation gain of the oscillation circuit 24 changes, whereby the output voltage of the oscillation circuit 24 changes. The comparison amplification circuit 25 compares the output voltage with the reference voltage to drive the output circuit 21 through the comparison amplification circuit 25. Accordingly, a detection signal is transmitted to the central control panel unit at a time point when the medical fluid amount of the drip chamber has been reduced to a given value.

Since the covers 11a and 11b are plated on the entire face, the electrodes 14a, 14b and the oscillation circuit 24 covered by the covers 11a and 11b are shielded. Accordingly, the electrostatic capacity between the electrodes 14a and 14b does not decrease due to approach of the human body, etc., and the influence of noise is reduced. Accordingly, no errors occur due to approach of the human body towards the electrodes and due to noise. Also, if shielding is realized through plating, the outer appearance is improved without increasing the number of the components and the weight.

Figure 6:
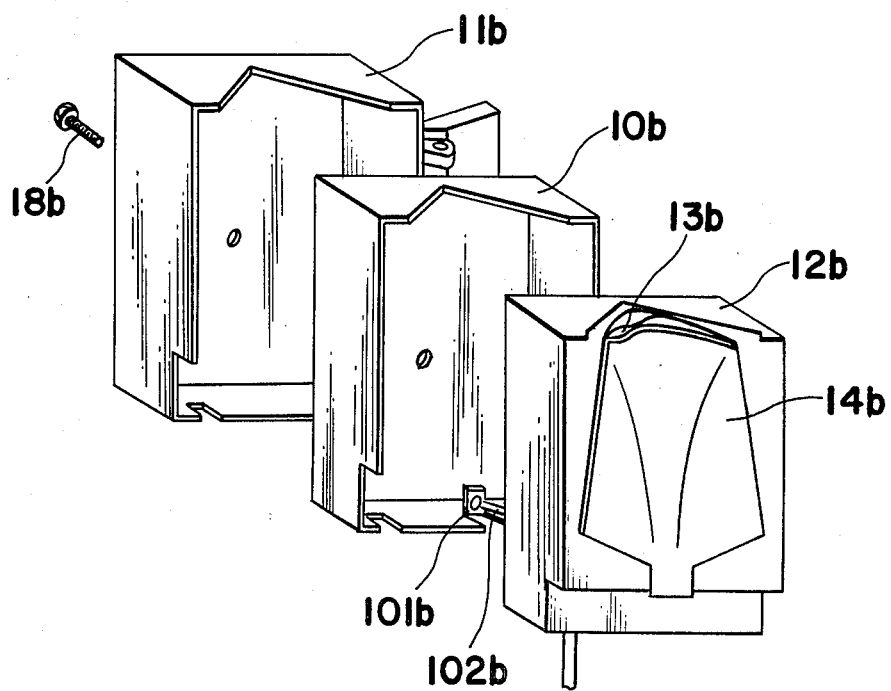
FIG. 6 is an exploded perspective view similar to FIG. 3 showing another embodiment of the parts of the level detector.

As another embodiment of the present invention as shown in, for example, FIG. 6, instead of the plating treatment, shield plates 10a; 10b (in FIG. 6, only the shield plate 10b is shown, but the same thing can be said about the shield plate 10a) may be provided between the covers 11a; 11b and the electrode fixtures 12a; 12b. In this case, a lead wire 102b for shielding is soldered to the connecting portion 101b of the shield plate 10b.

Figure 7:
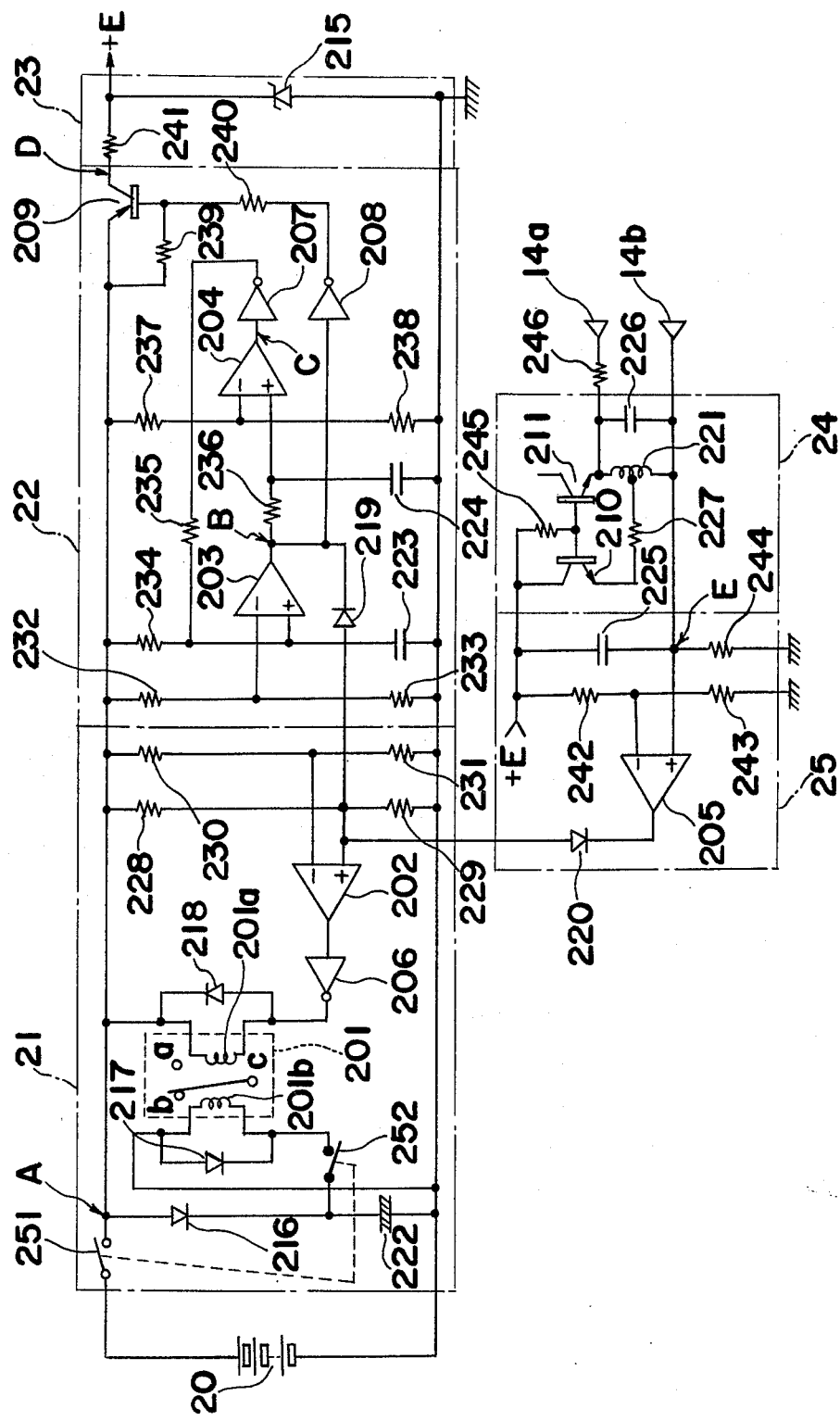
FIG. 7 is an electric circuit diagram showing the detailed construction of the circuit blocks of FIG. 5.

In addition, the circuit portion of FIG. 5 is construed in practical use, for instance, as shown with an electric circuit diagram of FIG. 7, which is operated in a manner as mentioned in detail hereinbelow. In FIG. 7, when the detection head 1 has been mounted on the drip chamber 8, the detecting operation of the dripping fluid level is made to operate after turning on a power supply switch 251, as shown in curve A of FIG. 8, and the voltage which has been set by resistors 232, 233 and the voltage which has been set by resistors 237, 238 are inputted to the respective negative side input terminals of differential amplifiers 203, or 204. Also, at the same time with the inputting operation, charging is made to a charging capacitor 223 through a resistor 234. The input voltage of the positive side input terminal of the differential amplifier 203 gradually rises. At the beginning, when the input voltage of the positive side input terminal of the differential amplifier 203 is smaller than the input voltage of the negative side input terminal, the output signal of the differential amplifier 203 is low level "L", as shown in curve B of FIG. 8. As a result, the output signal of a negative amplifier 208 becomes high level "H" and a transistor 209 is kept off. Accordingly, no voltage is applied to the constantvoltage circuit 23 and its subsequent voltages, as shown in curve D of FIG. 8, and the consumption current of all the circuits is small, for example, approximately 1 and 2 mA.

Figure 8:
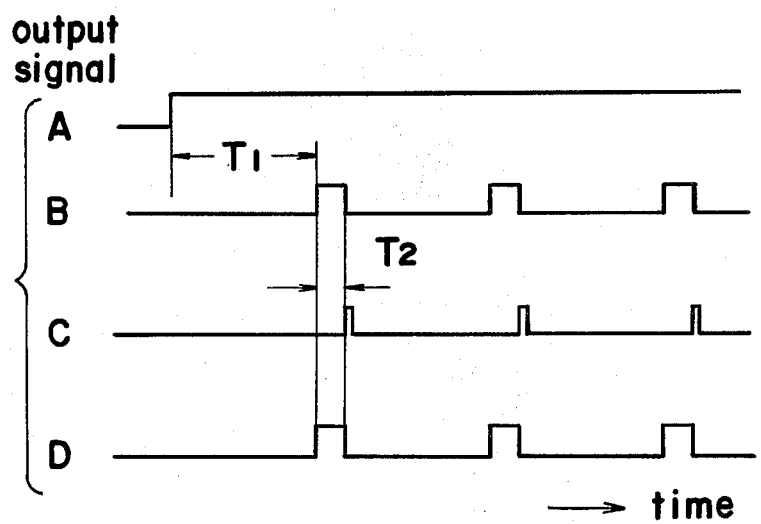
FIG. 8, is a time chart showing the signal wave forms generated at points A to D of FIG. 7.

When the charging of the capacitor 223 proceeds and the voltage of the positive side input terminal of the differential amplifier 203 is larger than the voltage of the negative input terminal after the lapse of a given time T1, the output reverses from the low level "L" to the high level "H", as shown in curve B of FIG. 8. As a result, the output of the negative amplifier 208 reverses the high level "H" to the low level "L". A transistor 209 turns "on" through bias resistors 239, 240 and the voltage is applied on the constantvoltage circuit 23 and its subsequent circuits as shown in curve D of FIG. 8. At this time, the consumption current of all the consumption of all the circuits is, for example, approximately 10 mA.

Also, when the differential amplifier 203 becomes high level "H", a charging capacitor 224 is charged through a resistor 236 and the voltage of the positive side input terminal of the differential amplifier 204 becomes higher than the voltage of the negative side input terminal. Thus, the output of the differential amplifier 204 becomes high level "H" from the low level "L" as shown in curve C of FIG. 8 and the output of a negative amplifier 207 becomes the low level "L" from the high level "H". As a result, the electric charge stored in the capacitor 223 is discharged through a resistor 235. The electric potential of the positive side input terminal of the differential amplifier 203 falls down to approximate 0 volt and the output reverses from the high level "H" to the low level "L" as shown in curve B of FIG. 8. Accordingly, the output of a negative amplifier 208 becomes high level "H" and the transistor 209 turns "off". The voltage is no longer applied to the constant-voltage circuit 23 and its subsequent circuits no more as shown in curve D of FIG. 8. Also, when the output of the differential amplifier 203 is the low level "L", the charging electric charge of the capacitor 224 is discharged through the resistor 236. The output of the differential amplifier 204 reverses to the low level "L" as shown in curve C of FIG. 8 and the output of the negative amplifier 207 becomes the high level "H" again. As a result, the capacitor 223 is charged again and thereafter the similar actions are repeated. As shown in curve D of FIG. 8, the voltage is intermittently applied upon the constant-voltage circuit 23. As the T1, for example, several tens seconds is made extremely larger than the T2, for example, one second or less, the consumption current of the total becomes extremely small.

When the voltage is applied upon the constant-voltage circuit 23, the constant voltage is applied upon the oscillation circuit 24 and the comparison amplification circuit 25 by a constant-voltage diode 215 and a current limiting resistor 241. The oscillation circuit 24 try to oscillate correspondingly and the comparison amplification circuit 25 drives the output circuit 21 according to this oscillation output.

One example where the detection is made when the electrostatic capacity of the electrodes 14a and 14b through the remaining amount of the medical fluid has become 4PF will be described hereinafter.

Figure 9:
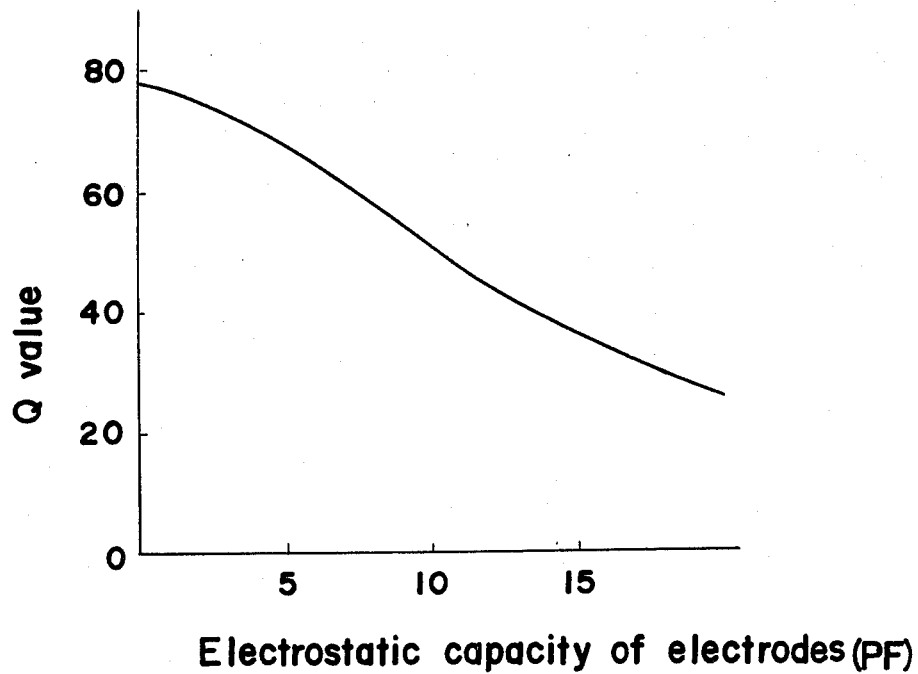
FIG. 9 is a graph showing the relationship between Q value of the resonance circuit of an oscillation circuit and the electrostatic capacity between electrodes employed within the circuit diagram of FIG. 7.

The oscillation circuit 24 is composed of transistors 210, 211, a tapped coil 221, a capacitor 226 and resistors 245, 246, 227. The electrostatic capacity of the electrodes 14a and 14b composes one portion of the LC resonance circuit of the oscillation circuit 24. Accordingly, the Q value of the resonance circuit changes in accordance with the electrostatic capacity between the electrodes 14a and 14b as shown in FIG. 9. The voltage dividing point voltage (hereinafter referred as to E-point voltage) of the capacitor 225 and resistor 244 of the comparison amplification circuit 25 changes, for example, as shown with a curve of FIG. 10 in accordance with the Q value. Namely, when the Q value increases and the oscillation is being performed, the impedance of the oscillation circuit 24 is kept reduced. Thus, the E-point voltage does not rise. On the other hand, when the Q value decreases and the oscillating operation stops, the impedance of the oscillation circuit 24 increases. Thus, the E-point voltage drops and is smoothed by the capacitor 225.

Figure 10:
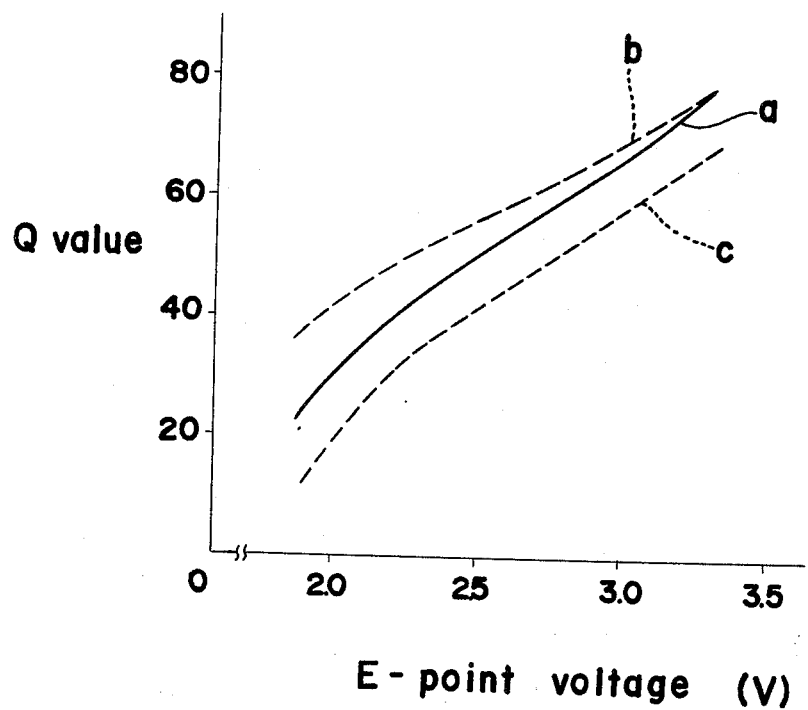
FIG. 10 is a graph showing the relationship between the Q value and the E-point voltage of the circuit diagram of FIG. 7.

The curves b and c of FIG. 10 shows the other two characteristics obtained by adjustment of each element constant of the oscillation circuit 24 in connection with the Q value and the E-point voltage.

The E-point voltage is inputted to the positive side input terminal of a differential amplifier 205. Voltage resistors 242, 243 are selected to the negative side input terminal of the differential amplifier 205 and approximately 3.1 volt is inputted thereto. Also, the connecting points of the dividing resistors 228 and 229 are connected with the positive side input terminal of the output circuit 202 and the voltage dividing voltages of the voltage dividing resistors 230, 231 are inputted to the negative side input terminal. The voltage dividing voltages of the voltage dividing resistors 228, 229 are adapted to become larger than the dividing voltages of the dividing voltage resistors 230 and 231.

When sufficient amount of medical fluid remains in the medical fluid bottle 5 and approximately the half portion of the drip chamber 8 is provided with the medical fluid, the electrostatic capacity between the electrodes 14a and 14b is larger above 4PF due to relatively large specific inductive capacity of the medical fluid. Accordingly, from FIG. 9 and FIG. 10, the E-point voltage is smaller than 3.1 volt. As a result, the output of the differential amplifier 205 is the low level "L" and the signal of the low level "L" is transmitted through the diode 220 to the positive side input terminal of the differential amplifier 202. Accordingly, the output of the differential amplifier 202 is the low level "L" and the output of the negative amplifier 206 is the high level "H". No current flows to the setting coil 201a of a latching relay 201. Accordingly, a contact c remains connected to a contact b as shown, thus resulting in no detection output produced.

As the dripping operation is performed for a longer period of time, the medical fluid of the medical fluid bottle 5 runs out and the medical fluid of the drip chamber 8 is being decreased. Since the electrodes 14a, 14b fit the drip chamber 8, the electrostatic capacity of the electrodes 14a, 14b considerably decreases correspondingly below the 4PF. Thus, as apparent from FIG. 9 and FIG. 10, the E-point voltage becomes larger than approximately 3.1 volt. As a result, the output of the differential amplifier 205 reverses to the high level "H". At this time, the power is supplied to the oscillation circuit 24, etc., and thus the output of the differential amplifier 203 of the timer circuit 22 should also be the high level "H". Accordingly, the voltage dividing voltages of the voltage dividing resistors 228, 229 are inputted to the positive side input terminal of the differential amplifier 202. Accordingly, the output of the differential amplifier 202 becomes the high level "H" and the output of the negative amplifier 206 becomes the low level "L". Thus, the current flows to a set coil 201a. As a result, a contact c is switched to a contact a to generate the detection output. The detection output is supplied to a centralized control portion 24 by signal cables 33 and 34.

Since the voltage applied to the constantvoltage circuit 23 is a pulse as shown in curve D of FIG. 8, the output of the low level "L" of the negative amplifier 206 is a pulse. However, once the latching relay 201 is driven, the condition is retained until the resetting operation is performed. Thus, inconveniences where the detection output is intermittently caused are avoided. A switch 251 is required to be turned off to perform resetting operation, and a switch 252 is turned on through operative cooperation with the switch action. The electric charge of a capacitor 222 which has been charged through the switch 251 and a diode 216 is discharged and current flows to the resetting coil 201b. As a result, the contact c is switched from the contact a to the contact b to stop the detection signal. The diode 216 prevents the charging electric charge of the capacitor 222 from flowing to the other circuit of the reset coil 201b of a latching relay 201 thereby to efficiently perform the resetting operation. Also, diodes 217, 218 are provided to absorb the surge of the coils 201b and 201a, respectively.

As described hereinabove about one embodiment, according to the present invention, the specific inductive capacity of the medical fluid is relatively large and hardly changes in types. Thus, a pair of electrodes are oppositely disposed about a given location of the medical fluid passage within medical fluid bottle to electrostatically detect the remaining amount of the medical fluid. Thus, no current flows to the medical fluid, so that no injury is inflicted on human body. Also, no error actions occur due to difference in medical fluid. In addition, attachment of a few drops on the detecting portion hardly changes the electrostatic capacity, thus resulting in no error actions and higher reliability. Also, since the sensitivity can be regulated and fixed during the manufacturing operation, the regulation is not required during usage and the handling operation is easier. Also, since there are no mechanical moving parts required for the detecting operation a longer life service is ensured. Also, the detecting portion can be grasped between the opposite electrodes, thus simplifying the engagement and disengagement of the detector itself.

Although the present invention is directed to a dripping fluid level detector comprising a pair of electrodes oppositely disposed around a given location of a supply passage of a medical fluid to be dripped, shield members to cover said pair of electrodes, and a detecting circuit to detect the remaining amount of the medical fluid according to changes in electrostatic capacity caused between said pair of electrodes, the present invention is not restricted only to the above-described embodiment. For example, the mounting position may be located in the transfusion tubes 7a, 7b or the medical fluid bottle 5. Or the detection head 1 may be variably changed in shape. Also, any circuit construction will do if only the electrostatic capacity between the electrodes 14a, 14b can be detected. Also, the shield members are formed either through metal plating or by metal plate. Such changes and modifications are to be included within the true scope of the present invention.

What is claimed is:

1. A dripping fluid level detector for use with a fluid passage of a medical fluid dropper comprising:

a drip chamber connected in said fluid passage;

a pair of electrodes oppositely disposed about and in contact with the outer surfaces of said drip chamber for detecting changes in the electrostatic capacity between said electrodes caused by changes in the amount of dripping fluid remaining in said chamber, said electrodes being formed of an elastic substance and being deformable into conformity with the shape of said drip chamber; and, an electric circuit for detecting a change in electrostatic capacity existing between said electrodes, which represents a change in the amount of fluid remaining in said chamber, said circuit including an oscillation circuit having an oscillation state which varies in accordance with a change in said electrostatic capacity and means responsive to said oscillator circuit for providing a predetermined output signal when said oscillator state reaches a predetermined condition indicating the dropping of fluid in said chamber below a predetermined amount.

2. A level detector as defined in claim 1, further comprising a pair of covers each supporting a respective one of said electrodes.

3. A level detector as defined in claim 2, wherein said pair of covers are hinged together in a manner permitting opening and closing of said covers to attach or release said electrodes from contact with said dripping chamber.

4. A level detector as defined in claim 3, wherein said covers are formed as a pair of pincers having a pair of holders provided with a spring means therebetween, said spring means biasing said covers into a closed condition surrounding said dripping chamber, said covers being supported thereby to said chamber and being opened by squeezing pressure applied to bring said holders together against the biasing force of said spring.

5. A level detector as defined in claim 4, further comprising a hangar provided on said holders for suspending said electrodes at a desired position.

6. A level detector as defined in claim 1, further comprising a pair of electrostatic shields each provided at the outside of a respective electrode.

7. A dripping level detector for use in a medical fluid passage of a liquid dropper comprising:

a drip chamber provided in said passage;

a pair of hinged covers formed as a pair of pincers having a pair of holders provided with a spring means therebetween, said covers being normally biased to a closing condition by said spring means to surround said drip chamber and being removable from said drip chamber upon opening said covers by pushing the holders towards one another against the force of said spring means;

a pair of electrodes each supported by a respective one of said covers for direct attachment with the outer surface of said drip chamber, said electrodes being made of an elastic substance deformable into conformity with the shape of said drip chamber;

an electric circuit for detecting a change in electrostatic capacity existing between said electrodes, which represents a change in the amount of fluid remaining in said chamber, said circuit including an oscillation circuit having an oscillation state which varies in accordance with a change in said electrostatic capacity and means responsive to said oscillator circuit for providing a predetermined output signal when said oscillator state reaches a predetermined condition indicating the dropping of fluid in said chamber below a predetermined amount;

a pair of electrostatic shield means each provided at the outside of a respective cover; and, means for suspending said covers supporting the electrodes at a desired position surrounding said drip chamber.

* * * * *